United States Patent [19]

Miyazawa et al.

[11] Patent Number: 4,822,917
[45] Date of Patent: Apr. 18, 1989

[54] PROCESS FOR THE HYDROFORMYLATION OF AN OLEFIN

[75] Inventors: Chihiro Miyazawa; Hiroshi Mikami; Akio Tsuboi; Katsuhide Hamano, all of Kurashiki, Japan

[73] Assignee: Mitsubishi Chemical Industries Limited, Tokyo, Japan

[21] Appl. No.: 133,807

[22] Filed: Dec. 16, 1987

[30] Foreign Application Priority Data

Dec. 23, 1986 [JP] Japan .................................. 61-307121
Dec. 26, 1986 [JP] Japan .................................. 61-313734
Oct. 7, 1987 [JP] Japan .................................. 62-252710
Oct. 8, 1987 [JP] Japan .................................. 62-253962

[51] Int. Cl.$^4$ ............................................. C07C 45/50
[52] U.S. Cl. ................................................... 568/454
[58] Field of Search ............................... 568/454, 451

[56] References Cited

U.S. PATENT DOCUMENTS

| | | | |
|---|---|---|---|
| 3,920,754 | 11/1975 | Wu et al. ............................... | 568/451 |
| 3,932,523 | 1/1976 | Strohmeyer et al. ................ | 568/451 |
| 3,954,877 | 5/1976 | Gipson .................................. | 568/454 |
| 4,221,743 | 7/1980 | Halstead et al. ..................... | 568/454 |
| 4,400,547 | 8/1983 | Dawes et al. ........................ | 568/454 |
| 4,528,403 | 7/1985 | Tano et al. ........................... | 568/454 |

FOREIGN PATENT DOCUMENTS

| | | | |
|---|---|---|---|
| 3017651 | 11/1980 | Fed. Rep. of Germany ...... | 568/454 |
| 3035468 | 4/1981 | Fed. Rep. of Germany ...... | 568/454 |
| 3338340 | 5/1984 | Fed. Rep. of Germany ...... | 568/454 |
| WO82/03856 | 11/1982 | PCT Int'l Appl. ................. | 568/454 |

*Primary Examiner*—Werren B. Lone
*Attorney, Agent, or Firm*—Oblon, Fisher, Spivak, McClelland & Maier

[57] ABSTRACT

A process for the hydroformylation of an olefin, which comprises hydroformylating an olefinic compound by reacting it with carbon monoxide and hydrogen in a hydroformylation reaction zone in the presence of a catalyst solution containing rhodium and an oxide of an organic trivalent phosphorus compound to form an aldehyde having a carbon number larger by one than that of the olefinic compound; adding an organic trivalent phosphorus compound to the reaction mixture, followed by distillation to separate a distillate containing the aldehyde from a high-boiling residue containing rhodium; oxidizing the high-boiling residue at the same time as or subsequent to the distillation to convert the organic trivalent phosphorus compound to its oxide; and recycling the oxidized residue to the hydroformylation reaction zone as a recycling catalyst solution, wherein the hydroformylation reaction is conducted under a condition such that the proportion of an alcohol content supplied as contained in the recycling catalyst solution is maintained at a level of not higher than 14% by weight based on the total amount of the olefinic compound and the catalyst solution supplied to the hydroformylation reaction zone.

11 Claims, No Drawings

PROCESS FOR THE HYDROFORMYLATION OF AN OLEFIN

The present invention relates to a process for the hydroformylation of an olefin. More particularly, the present invention relates to a process for controlling the formation of high-boiling byproducts during the hydroformylation reaction of an olefin.

It is well known to produce an aldehyde by the hydroformylation of an olefinic compound by reacting the olefinic compound with carbon monoxide and hydrogen in the presence of a catalyst. In particular, for the hydroformylation of a branched olefinic compound, a process has been proposed which comprises conducting the hydroformylation reaction by using a rhodium catalyst modified with an oxide of an organic trivalent phosphorus compound, separating the resulting reaction product by distillation and obtaining the formed aldehyde as a distillate, whereas the residue containing the rhodium catalyst is recycled to the hydroformylation reaction system (Japanese Unexamined Patent Publication No. 76034/1984).

However, if the hydroformylation reaction is conducted continuously for a long period of time in accordance with the above proposed process, formation of high-boiling byproducts produced during the hydroformylation reaction such as a trimer of the formed aldehyde or an acetal, gradually increases, whereby the yield of the aldehyde decreases and the high-boiling byproducts accumulate in the recycling catalyst solution, thus eventually leading to a problem such that the operation will be impossible by an apparatus with a limited capacity. These problems may be solved by withdrawing a recycling catalyst solution out of the system depending upon the production of the high-boiling byproducts and supplying to the system afresh a catalyst corresponding to the amount of the catalyst withdrawn from the system. However, if the production of the high-boiling byproducts is substantial during the hydroformylation reaction, and the catalyst solution withdrawn from the system will correspondingly be substantial, the cost for recovering the catalyst from the withdrawn catalyst solution (the catalyst recovery cost) will increase, such being disadvantageous from the industrial point of view.

The present inventors have conducted extensive research on a method for suppressing the high-boiling byproducts during the hydroformylation reaction in order to solve the above-mentioned problems inherent to the conventional technique and as a result, have found that the production of the high-boiling byproducts can remarkably be reduced by conducting the hydroformylation reaction while maintaining the proportion of the alcohol supplied from the recycling catalyst solution relative to the total charge of the olefinic compound and the catalyst solution supplied to the hydroformylation reaction system at a level of not higher than a certain specific proportion. The present invention has been accomplished on the basis of this discovery.

It is therefore the object of the present invention to provide a hydroformylation process whereby the production of the high-boiling byproducts is suppressed during the hydroformylation reaction of an olefin by means of a rhodium catalyst.

In the broadest aspect, the present invention provides a process for the hydroformylation of an olefin, which comprises hydroformylating an olefinic compound by reacting it with carbon monoxide and hydrogen in a hydroformylation reaction zone in the presence of a catalyst solution containing rhodium and an oxide of an organic trivalent phosphorus compound to form an aldehyde having a carbon number larger by one than that of the olefinic compound; adding an organic trivalent phosphorus compound to the reaction mixture, followed by distillation to separate a distillate containing the aldehyde from a high-boiling residue containing rhodium; oxidizing the high-boiling residue at the same time as or subsequent to the distillation to convert the organic trivalent phosphorus compound to its oxide; and recycling the oxidized residue to the hydroformylation reaction zone as a recycling catalyst solution, wherein the hydroformylation reaction is conducted under a condition such that the proportion of an alcohol content supplied as contained in the recycling catalyst solution is maintained at a level of not higher than 14% by weight based on the total amount of the olefinic compound and the catalyst solution supplied to the hydroformylation reaction zone.

Now, the present invention will be described in detail with reference to the preferred embodiments.

In the process of the present invention, the hydroformylation reaction of the first step is conducted by a usual method. Namely, the hydroformylation reaction is conducted by supplying an olefinic compound and carbon monoxide and hydrogen to a hydroformylation reaction zone where a catalyst solution containing rhodium and an oxide of an organic trivalent phosphorus compound is present, to form an aldehyde having a carbon number larger by one than that of the olefinic compound. As the catalyst solution, a high-boiling residue containing rhodium which is obtained by a distillation step and recycled in the recycling step, as described hereinafter, is used. However, if necessary, the catalyst may be supplied afresh. The fresh catalyst may be prepared in the reaction system in accordance with a usual method by adding a rhodium compound and, if necessary, an oxide of an organic trivalent phosphorus compound to the hydroformylation reaction zone. However, it is preferred that the rhodium compound and the oxide of an organic trivalent phosphorus compound are first mixed in a solvent, and the mixture is subjected to activating treatment with carbon monoxide, whereupon the treated mixture is added to the reaction system.

As the rhodium compound to be used for the preparation of the catalyst, there may be mentioned an inorganic acid salt such as rhodium nitrate or rhodium sulfate; an organic acid salt such as rhodium acetate, sodium rhodium oxalate or potassium rhodium malate; and an amine complex salt such as $[RhL_6]X_3$, $[RhL_5(H_2O)]X_3$, $[RhL_5(OH)]X_2$, $[RhL_5(NO_2)]X_2$ or $[Rh(Py)_3(NO_3)_2]$ where X is $NO_3^-$, $OH^-$ or $\frac{1}{2}(SO_4^{2-})$, L is $NH_3$ and Py is pyridine. Among them, rhodium nitrate and rhodium acetate are preferably used.

As the oxide of an organic trivalent phosphorus compound, there may be used an arylphosphine oxide such as triphenylphosphine oxide, tritolylphosphine oxide or trianisylphosphine oxide; an alkylphosphine oxide such as tributylphosphine oxide or trioctylphosphine oxide; or an alkylarylphosphine oxide containing both alkyl and aryl groups. Further, there may be used an arylphosphite oxide such as triphenylphosphite oxide (i.e. triphenyl phosphate) or tritolylphosphite oxide; an alkylphosphite oxide such as triethylphosphite oxide, tripropylphosphite oxide or tributylphosphite oxide; or an alkylarylphosphite oxide containing both alkyl and aryl groups. Furthermore, it is possible to use an oxide of a multidentate ligand phosphine such as bis(diphenylphosphino)methane dioxide, 1,2-bis(diphenylphosphino)ethane dioxide, 1,4-bis(diphenylphosphino)butane dioxide, 1,2-bis(diphenylphosphinomethyl)cyclobutane dioxide or 2,3-O-isopropylidene-2,3-dihydroxy-1,4-bis(diphenylphosphino)butane dioxide.

Such an oxide of an organic trivalent phosphorus compound is preferably used in such an amount that phosphorus in the form of an oxide is present in the hydroformylation reaction zone in a concentration of at least 1 atom, usually from 1 to 1,000 atoms, preferably from 10 to 1,000 atoms, more preferably from 10 to 500 atoms, per atom of rhodium.

Further, when an active catalyst is preliminarily prepared from the rhodium compound and the oxide of an organic trivalent phosphorus compound, both materials may preferably be mixed in the above-mentioned ratio and then treated with carbon monoxide. The treating conditions may optionally be selected within such ranges that the carbon monoxide partial pressure is from 1 to 200 kg/cm$^2$, preferably from 1 to 10 kg/cm$^2$, the temperature is from 10 to 200° C., preferably from 20° to 150° C. and the treating time is from 1 to 100 minutes, preferably from 2 to 50 minutes. In this case, it is preferred to use carbon monoxide which does not substantially contain hydrogen.

The catalyst concentration in the reaction zone is usually from 1 to 500 mg/liter, preferably from 2 to 100 mg/liter, as rhodium.

As the olefinic compound to be used for the hydroformylation reaction, there may be mentioned a straight chain α-olefin having not more than 30 carbon atoms such as ethylene, propylene, 1-butene, 1-pentene, 1-hexene, 1-octene or 1-decene; a straight chain internal olefin such as 2-butene, 2-pentene, 2-hexene, 3-hexene, 2-octene or 3-octene; a branched α-olefin such as isobutylene, 2-methyl-1-butene, 2-methyl-1-pentene, 3-methyl-1-pentene, 2-methyl-1-hexene, 3-methyl-1-hexene, 2-methyl-1-heptene, 3-methyl-1-heptene or 4-methyl-1-heptene; a multi branched α-olefin such as 2,3-dimethyl-1-butene, 2,3-dimethyl-1-pentene, 2,4-dimethyl-1-pentene, 2,3-dimethyl-1-hexene, 2,4-dimethyl-1-hexene, 2,5-dimethyl-1-hexene or 3,4-dimethyl-1-hexene; and double bond isomers thereof.

Further, there may also be used a mixture of isomers such as dimers, trimers or tetramers of e.g. propylene, butene or isobutylene, or an olefin having a substituent such as allyl alcohol, acrolein acetal, vinyl acetate, styrene or an alkylvinyl ether.

The present invention is particularly advantageous when applied to the hydroformylation of octenes obtained by dimerization of a C$_4$ fraction (hereinafter referred to as a BB fraction) obtainable in a large amount by thermal decomposition of naphtha or by catalytic decomposition of heavy or light oil. Because, as opposed to the case where the rhodium catalyst modified with an organic phosphine is used, the reaction can readily be conducted according to the present invention wherein the oxide of the organic trivalent phosphorus compound is used even when these branched internal olefins or mixtures of isomers mainly composed of branched internal olefins are used as the starting materials.

As the solvent, any optional solvent may be used so long as it is capable of dissolving the catalyst and does not adversely affect the reaction. For instance, there may be used an aromatic hydrocarbon such as benzene, toluene, xylene or dodecylbenzene, an alicyclic hydrocarbon such as cyclohexane; an ether such as dibutyl ether, ethylene glycol dimethyl ether, diethylene glycol diethyl ether, triethylene glycol dimethyl ether or tetrahydrofuran; or an ester such as diethylphthalate, dioctylphthalate or bis(2-ethylhexyl)phthalate. Further, an aldehyde formed by the hydroformylation reaction may also be used as the solvent.

From the viewpoint of the reaction rate, it is advantageous that the reaction temperature is high. However, if the reaction temperature is too high, it is likely that the catalyst will decompose. Accordingly, it is usually preferred to conduct the reaction at a temperature of from 50° to 170° C., particularly from 100° to 150° C.

As the carbon monoxide and hydrogen gas, it is preferred to use a water gas wherein the molar ratio of hydrogen to carbon monoxide is from 1/5 to 5/1, particularly from $\frac{1}{2}$ to 2/1. The partial pressure of the water gas is preferably from 20 to 500 kg/cm$^2$, particularly from 50 to 300 kg/cm$^2$.

The reaction can be conducted in a continuous system or in a batch system.

In the process of the present invention, the hydroformylation reaction is conducted under a condition such that the proportion of the content of the alcohol supplied as contained in the recycling catalyst solution (hereinafter referred to as the alcohol content supplied from the recycling catalyst solution) is maintained at a level of not higher than 14% by weight, preferably not higher than 10% by weight, more preferably not higher than 5% by weight, based on the total amount (hereinafter referred to as the charge amount) of the olefinic compound (including the olefinic compound supplied afresh and the olefinic compound recycled) and the catalyst solution (including the catalyst solution supplied afresh and the catalyst solution recycled) supplied to the hydroformylation reaction zone. The alcohol to be controlled by the present invention is an alcohol produced by the hydrogenation of the aldehyde formed by the hydroformylation reaction of an olefinic compound as the starting material (i.e. an alcohol corresponding to the formed aldehyde).

In the continuous operation of a hydroformylation reaction plant, at the initiation of the operation or during a limited period at the initial stage of the operation, it is possible that the catalyst solution contains no substantial alcohol, or the alcohol content supplied from the recycling catalyst solution is not higher than 14% by weight based on the charge amount. The process of the present invention does not cover such a case. However, even in such a case, if the operation is continuously conducted under the usual working conditions for an industrial hydroformylation reaction without adjusting the alcohol content, it is usual that more than 14% by weight of the alcohol accumulates in the recycling catalyst solution usually in one day or so, whereupon the control by the process of the present invention can effectively be employed.

If the proportion of the alcohol content supplied from the recycling catalyst solution exceeds 14% by weight based on the above-mentioned charge amount, there will be a substantial increase in the formation of high-boiling byproducts during the hydroformylation reaction, such as a self condensation product of the formed aldehyde such as a dimer or trimer thereof, or acetals, and the yield of the formed aldehyde decreases, such being undesirable.

As a method for controlling the proportion of the alcohol content, there may be mentioned a method wherein when the aldehyde is separated by distillation from the reaction product solution obtained by the hydroformylation reaction, the distillation conditions are selected so that the alcohol concentration in the residual solution will be at a level of not higher than the specific concentration, or a method wherein a part of the recycling catalyst solution is withdrawn for the adjustment, or a method wherein the ratio of the amount of the olefin charged (supplied) to the amount of the recycling catalyst solution is adjusted.

In the process of the present invention, an organic trivalent phosphorus compound is added to the reaction solution obtained in the step of the hydroformylation reaction, followed by distillation to distill the aldehyde or alcohol formed by the reaction.

As the organic trivalent compound, it is preferred to use the one which corresponds to the oxide of an organic trivalent phosphorus compound present in the catalyst solution for the hydroformylation reaction. Usually, triphenylphosphine or tributylphosphine is suitably used. The organic trivalent phosphorus compound will establish a coordination with the rhodium catalyst in the reaction mixture and thus serves to stabilize the rhodium catalyst. The organic trivalent phosphorus compound is added in such an amount that the phosphorus in a trivalent state is at least one atom per atom of rhodium. However, even when the organic trivalent phosphorus compound is used in a large amount, the stability of the catalyst does not necessarily increase in proportion to the added amount. Therefore, the phosphorus compound is added usually in such an amount that the phosphorus in the trivalent state is from 1 to 100 atoms, preferably from 1 to 20 atoms, per atom of rhodium.

The hydroformylation reaction mixture thus added with the organic trivalent phosphorus compound is subjected to distillation in a usual manner to separate a distillate having a low boiling point such as an aldehyde or alcohol from the residue having a high boiling point containing rhodium. The rhodium catalyst in the reaction mixture is stabilized by the organic trivalent phosphorus compound, and accordingly an optional distillation system such as a flush distillation, a normal pressure distillation, a reduced pressure distillation or a combination thereof may be employed. The distillation temperature is preferably not higher than 200°C., particularly from 25° to 150° C.

The residue i.e. the bottom of the above distillation step contains high boiling substances such as the rhodium catalyst and the organic trivalent phosphorus compound. In the process of the present invention, the residue is oxidized at the same time as or subsequent to this distillation to convert the organic trivalent phosphorus compound to its oxide, and the oxidized residue is recycled as a recycling catalyst solution to the hydroformylation reaction zone.

In the case where the residue is oxidized at the same time as the distillation, the distillation may be conducted in the presence of molecular oxygen such as air to oxidize the residue. Namely, by conducting the distillation while introducing a small amount of molecular oxygen such as air into the distillation tower, the distillation and the oxidation of the organic trivalent compound can be conducted simultaneously. For example, even in a reduced pressure distillation tower, a certain amount of air usually leaks in, and the oxidation of the organic trivalent phosphorus compound proceeds even with the air in such an amount. If the oxidation in the tower is not sufficient, the high-boiling residue discharged as the bottom may again be oxidized with air in the manner as described below.

In the case where the high-boiling residue is oxidized after the distillation, a method of oxidizing in the presence of molecular oxygen or a method of oxidizing in the presence of a peroxide may be employed. This treatment is intended to convert the organic trivalent phosphorus compound in the high-boiling residue to the corresponding oxide. However, it is not necessary to completely convert all the organic trivalent phosphorus compound to the corresponding oxide.

The oxidation in the presence of molecular oxygen may be conducted by blowing molecular oxygen, usually atmospheric air, into the high-boiling residue. The oxidation conditions are suitably selected from a temperature of from 20° to 200° C., preferably from 20° to 150° C. and a time of from one minute to 5 hours, preferably from 5 minutes to 2 hours.

The oxidation in the presence of a peroxide may be conducted by (1) a method wherein a peroxide is added to the high-boiling residue to convert the organic trivalent phosphorus compound to the corresponding oxide, and the oxidized residue is then recycled as a recycling catalyst solution to the hydroformylation reaction zone, or (2) a method wherein the high-boiling residue is recycled together with a peroxide to the hydroformylation reaction zone. The method (2) is preferred.

The method (1) is conducted usually at a temperature of from 0° to 150° C., preferably from 0° to 100° C., for from 1 minute to 100 hours, preferably from 1 minute to 10 hours. The treated solution composed of the oxidized high-boiling residue is recycled to the hydroformylation reaction zone and used as the catalyst solution or a part thereof.

In the method (2), the high-boiling residue may simply be recycled together with the below-mentioned peroxide to the hydroformylation reaction zone. However, it is preferred that the peroxide is added and mixed with the high-boiling residue containing rhodium, and then the mixture is recycled to th hydroformylation reaction zone. In this case, the organic trivalent phosphorus compound in the high-boiling residue can be converted to the corresponding oxide while the mixture is being recycled. However, it is not necessarily required to completely convert the organic trivalent phosphorus compound to the corresponding oxide before the mixture is recycled to the hydroformylation reaction zone. For example, a part of the peroxide may be supplied to the hydroformylation reaction zone separately from the high-boiling residue containing rhodium, and the additional oxidation of the organic trivalent phosphorus compound may be conducted in the reaction zone.

As the peroxide, for example, benzoyl peroxide, t-butyl peroxide, lauroyl peroxide or hydrogen peroxide may be employed. It is preferred to employ a peroxide formed by the oxidation of an olefinic compound, particularly an olefinic compound used as the starting material for the hydroformylation reaction, with molecular oxygen such as air. Namely, when molecular oxygen such as air is blown into the olefinic compound as the starting material, a part of the olefinic compound is converted to a peroxide. It is preferred that the olefinic compound containing such a peroxide is added as it is to the high-boiling residue containing rhodium and mixed therewith, and then the mixture is supplied to the hydroformylation reaction zone to conduct the hydroformylation reaction. The peroxide content in the olefinic compound may be quantitatively analyzed, for example, by adding an excess amount of ferrous thiocyanate to the olefinic compound so that ferrous ions are oxidized by the peroxide to ferric ions and measuring the amount of the formed ferric thiocyanate by colorimetry.

The amount of the peroxide to be used is an amount necessary to oxidize and convert the organic trivalent phosphorus compound contained in the high-boiling residue to its oxide. Accordingly, at least 2 equivalent of the peroxide is employed relative to 1 mol of the organic trivalent phosphorus compound added in the distillation step. Usually, from 5 to 20 equivalent of the peroxide is employed relative to 1 mol of the organic trivalent phosphorus compound. (Here, 1 equivalent of the peroxide is meant for the amount capable of oxidizing 1 mol of Fe(II) to Fe(III) in the above-mentioned quantitative analysis.) However, it is dangerous to use the peroxide in a great amount beyond the required amount, and such an excessive amount must be avoided also because the yield of the aldehyde may thereby be deteriorated. Further, in the high-boiling residue, high-boiling byproducts and phosphorus compounds produced by side reactions tend to accumulate, and accordingly it is preferred to continuously or intermittently discharge a part of them out of the reaction zone to maintain their concentration in the reaction zone to be constant.

Now, the present invention will be described in further detail with reference to Examples. However, it should be understood that the present invention is by no means restricted by these specific Examples.

EXAMPLES 1 to 4 and COMPARATIVE EXAMPLES 1 to 3

(1) Preparation of olefin starting material

A $C_4$ fraction (composed of 6% by weight of isobutene, 43% by weight of 1-butene, 25% by weight of 2-butene, 25% by weight of butanes and 1% by weight of others) obtained by removing butadiene and isobutene from a BB fraction obtained from a cracker of naphtha, was dehydrated by molecular sieve 13X. Then, 4 kg of the dehydrated $C_4$ fraction, 5.5 g of a n-hexane solution of nickel octanoate (Ni content: 6% by weight) and 11.3 g of ethylaluminum dichloride were charged under a nitrogen atmosphere to an induction agitation-type SUS autoclave having an internal capacity of 10 liters, and the mixture was reacted at 40° C. for 7 hours.

After the reaction, 340 g of a 5 wt % $H_2SO_4$ aqueous solution was added to the mixture to deactivate the catalyst, and then the mixture was subjected to liquid-liquid separation, followed by distillation under atmospheric pressure to obtain a $C_8$ olefin mixture (hereinafter referred to as an octene mixture).

The above reaction and distillation were repeated three times.

(2) Hydroformylation reaction

Into an induction agitation-type SUS-316 autoclave having an internal capacity of 10 liters, 7 liters of the octene mixture obtained in the above step (1) and a methanol solution of rhodium acetate (rhodium concentraion: 4,000 mg/liter) in an amount to bring the rhodium concentration in the reaction solution to 10 mg/liter, were added. Further, triphenylphosphine oxide in an amount of 20 mol times relative to the rhodium was added thereto, and the autoclave was sealed. The autoclave was flushed with nitrogen gas, and the nitrogen gas was pressurized upto 40 kg/cm²G and then released to atmospheric pressure. This operation was repeated three times, and then the temperature was raised to 130° C. Immediately after the temperature reached 130° C., water gas ($H_2/CO=1$) was introduced under pressure to bring the total pressure to a level of 170 kg/cm²G, and the reaction was conducted at 130° C. for 6 hours. During this period, water gas was supplemented from an accumulator via a constant pressure control apparatus to compensate the water gas consumed by the reaction, whereby the autoclave was maintained under a pressure of 170 kg/cm²G. After the completion of the reaction, the reaction solution was analyzed by gas chromatography, whereby the yield of $C_9$-aldehyde was 92.72%, the yield of $C_9$-alcohol was 4.90%, and the yield of high-boiling byproducts was 0.40%.

(3) Distillation of the reaction solution of the hydroformylation reaction

To the reaction solution of the hydroformylation reaction obtained in the above step (2), triphenylphosphine was added in an amount of 9 mol times relative to the rhodium in the reaction solution. Then, mixture was distilled in an air atmosphere under a pressure of 70 mmHg at a tower top temperature of 110° C. to distill the aldehyde, whereby a distillation residue containing an alcohol as the bottom was obtained. This distillation residue was maintained under atmospheric pressure in an air atmosphere at 140° C. for 2 hours for oxidation treatment to obtain a treated solution (hereinafter referred to as a recycling catalyst solution A).

Further, a part of the recycling catalyst solution A was distilled under reduced pressure in a nitrogen atmosphere at a pressure of 30 mmHg at a tower top temperature of 115° C. to distill about 90% by weight of the alcohol contained and to obtain the residue (hereinafter referred to as a recycling catalyst solution B).

(4) Hydroformylation reaction by the recycling catalyst solution

Into a top and bottom agitation-type SUS-316 autoclave having an internal capacity of 200 ml, the octene mixture obtained in the above step (1) and the recycling catalyst solution A or B obtained in the above step (3) were introduced in the proportions as shown in Table 1, and then the autoclave was sealed. The autoclave was flushed with nitrogen gas. Then, the nitrogen gas was pressurized to a level of 40 kg/cm²G and then released to atmospheric pressure. This operation was repeated three times, and then the temperature was raised to 130° C. Immediately after the temperature reached 130° C., water gas ($H_2/CO=1$) was introduced under pressure to bring the total pressure to 170 kg/cm²G, and the reaction was conducted at 130° C. until the convertion of the octene mixture exceeded 95%. During this period, water gas was supplemented from an accumulator via a constant pressure control apparatus to compensate the water gas consumed by the reaction, whereby the autoclave was maintained under a pressure of 170 kg/cm²G. After the completion of the reaction, the reaction solution was analyzed by gas chromatography.

The alcohol concentration in the charge (i.e. the proportion of the alcohol content supplied from the recycling catalyst solution relative to the charge amount) and the yield of the aldehyde, the yield of the alcohol and the yield of high-boiling byproducts after the reaction are shown in Table 1.

EXAMPLE 5

(1) Preparation of olefin starting material

The octene mixture was prepared in the same manner as in the step (1) in Example 1.

(2) Hydroformylation reaction

The hydroformylation reaction was conducted in the same manner as in the step (2) in Example 1.

(3) Oxidation treatment by the distillation of the hydroformylation reaction solution To the hydroformylation reaction solution obtained in the above step (2), triphenylphosphine was added in an amount of 6 mol times relative to the rhodium in the reaction solution, and continuous rectification was conducted under the conditions given below. Triphenylphosphine was subjected to oxidation treatment during the rectification to obtain a treated solution as the bottom (hereinafter referred to as a recycling catalyst solution C). The alcohol content was 10% by weight. The conditions for the continuous rectification were as follows:

Pressure: 120 mmHg, tower bottom temperature: 140° C.,
Retention time of the bottom: 4.0 hours,
Amount of air leaked in: As oxygen, 10 mol times of triphenylphosphine (4) Hydroformylation reaction by the recycling catalyst solution The hydroformylation reaction was conducted in the same manner as in the step (4) in Example 1 except that the recycling catalyst solution C obtained in the above step (3) was used as the recycling catalyst solution. The results are shown in Table 1.

EXAMPLE 6

(1) Preparation of olefin starting material

The octene mixture was prepared in the same manner as in the step (1) in Example 1.

(2) Hydroformylation reaction

The hydroformylation reaction was conducted in the same manner as in the step (2) in Example 1.

(3) Distillation of the hydroformylation reaction solution

To the hydroformylation reaction solution obtained in the above step (2), triphenylphosphine was added in an amount of 9 mol times relative to the rhodium in the reaction solution, and the mixture was subjected to distillation in a nitrogen gas atmosphere under a pressure of 70 mmHg at the tower top temperature of 110° C. to distill the aldehyde, whereby a distillation residue containing an alcohol was obtained as the bottom.

(4) Oxidation treatment of the distillation residue

The distillation residue obtained in the above step (3) was maintained under atmospheric pressure in an air atmosphere at 140° C. for 6 hours for oxidation treatment to obtain a treated solution (hereinafter referred to as a recycling catalyst solution D).

(5) Hydroformylation reaction by the recycling catalyst solution

The hydroformylation reaction was conducted in the same manner as in the step (4) in Example 1 except that the recycling catalyst solution D obtained in the above step (4) was used as the recycling catalyst solution. The results are shown in Table 1.

TABLE 1

| | Recycling catalyst solution used for the reaction | Volume ratio of the octene mixture to the recycling catalyst solution | Alcohol content in the charge (wt %) | Yield (wt %) | | |
|---|---|---|---|---|---|---|
| | | | | $C_9$—aldehyde | $C_9$—alcohol | high-boiling byproducts |
| Example 1 | A | 20 | 4.2 | 91.0 | 5.1 | 1.6 |
| Example 2 | B | 20 | 2.1 | 91.5 | 4.2 | 1.3 |
| Example 3 | B | 4 | 8.9 | 88.9 | 4.5 | 2.5 |
| Example 4 | B | 3 | 11.2 | 88.4 | 4.3 | 3.5 |
| Example 5 | C | 4 | 2.0 | 91.0 | 4.9 | 1.4 |
| Example 6 | D | 25 | 3.2 | 90.0 | 4.5 | 1.5 |
| Comparative Example 1 | A | 4 | 17.8 | 83.0 | 4.3 | 8.7 |
| Comparative Example 2 | A | 3 | 22.8 | 77.8 | 4.4 | 13.2 |
| Comparative Example 3 | B | 1.5 | 17.9 | 82.5 | 4.5 | 8.9 |

EXAMPLES 7 to 10 and COMPARATIVE EXAMPLES 4 to 6

(1) Preparation of olefin starting material

The octene mixture was prepared in the same manner as in the step (1) in Example 1.

(2) Hydroformylation reaction

The hydroformylation reaction was conducted in the same manner as in the step (2) in Example 1.

(3) Distillation of the hydroformylation reaction solution

To the hydroformylation reaction solution obtained in the above step (2), triphenylphosphine was added in an amount of 9 mol times relative to the rhodium in the reaction solution, and the mixture was subjected to distillation under a nitrogen gas atmosphere at a pressure of 70 mmHg at a tower top temperature of 110° C. to distill the aldehyde, whereby a distillation residue containing an alcohol was obtained as the bottom.

(4) Oxidation treatment of the distillation residue

To the distillation residue obtained in the above step (3), a solution obtained by blowing an air into the octene mixture obtained in the above step (1) to form a peroxide (peroxide content: 130 meq/liter) was added in an amount to bring the peroxide content to 5 equivalent relative to 1 mol of triphenylphosphine in the distillation residue, and the mixture was maintained in a nitrogen atmosphere at 40° C. for 30 minutes for oxidation treatment to obtain a treated solution (hereinafter referred to as a recycling catalyst solution A').

Further, a part of the recycling catalyst solution A' was distilled under reduced pressure in a nitrogen atmosphere at a pressure of 30 mmHg at a tower top temperature of 115° C. to distill 90% by weight of the alcohol contained and to obtain a residue as the bottom (hereinafter referred to as a recycling catalyst solution B').

(5) Hydroformylation reaction by the recycling catalyst solution

Into a top and bottom agitation-type SUS-316 autoclave having an internal capacity of 200 ml, the octene mixture obtained in the above step (1) and the recycling catalyst solution A' or B' obtained in the above step (4) were introduced in the proportions as identified in Table 2, and the autoclave was sealed. The autoclave was flushed with nitrogen gas, and the nitrogen gas was pressurized up to 40 kg/cm$^2$G and then released to atmospheric pressure. This operation was repeated three times, and then the temperature was raised to 130° C.. Immediately after the temperature reached 130° C., water gas ($H_2/CO=1$) was introduced under pressure to bring the total pressure to a level of 170 kg/cm$^2$G, and the reaction was conducted at 130° C. until the convertion of the octene mixture exceeded 95%. During this period, water gas was supplemented from an accumulator via a constant pressure control apparatus to compensate the water gas consumed by the reaction, whereby the autoclave was maintained under a pressure of 170 kg/cm$^2$G. After the completion of the reaction, the reaction mixture was analyzed by gas chromatography. The alcohol concentration in the charge (the proportion of the alcohol content supplied from the recycling catalyst solution relative to the charge amount) and the yield of the aldehyde, the yield of the alcohol and the yield of high-boiling byproducts, after the reaction, are shown in Table 2.

As is evident from the foregoing Examples, according to the process of the present invention, it is possible to effectively suppress the formation of high-boiling byproducts during the hydroformylation reaction of an olefin.

We claim:

1. A process for the hydroformylation of an olefin, which comprises hydroformylating an olefinic compound by reacting it with carbon monoxide and hydrogen in a hydroformylation reaction zone in the presence of a catalyst solution containing rhodium and an oxide of an organic trivalent phosphorus compound to form an aldehyde having a carbon number larger by one than that of the olefinic compound; adding an organic trivalent phosphorus compound to the reaction mixture, followed by distillation to separate a distillate containing the aldehyde from a high-boiling residue containing rhodium; oxidizing the high-boiling residue at the same time as or subsequent to the distillation to convert the organic trivalent phosphorus compound to its oxide; and recycling the oxidized residue to the hydroformylation reaction zone as a recycling catalyst solution, the improvement wherein the hydroformylation reaction is conducted under such condition that the proportion of alcohol supplied in the recycling catalyst solution is maintained at a level not higher than 14% by weight based on the total amount of the olefinic compound and the catalyst solution supplied to the hydroformylation reaction zone.

2. The process according to claim 1, wherein the high-boiling residue is oxidized at the same time as the distillation to convert the organic trivalent phosphorus compound to its oxide.

3. The process according to claim 2, wherein the distillation is conducted in the presence of molecular oxygen to oxidize the high-boiling residue and to convert the organic trivalent phosphorus compound to its oxide.

4. The process according to claim 1, wherein the high-boiling residue is oxidized subsequent to the distillation to convert the organic trivalent phosphorus compound to its oxide.

5. The process according to claim 4, wherein the high-boiling residue is oxidized in the presence of molecular oxygen subsequent to the distillation.

6. The process according to claim 4, wherein the high-boiling residue is oxidized in the presence of a peroxide subsequent to the distillation.

7. The process according to claim 6, wherein the high-boiling residue is recycled to the hydroformylation reaction zone as a recycling catalyst solution together with the peroxide, subsequent to the distillation.

8. The process according to claim 7, wherein the high-boiling residue and the peroxide are mixed before being recycled to the hydroformylation reaction zone.

TABLE 2

| | Recycling catalyst solution used for the reaction | Volume ratio of the octene mixture to the recycling catalyst solution | Alcohol content in the charge (wt %) | Yield (wt %) | | |
|---|---|---|---|---|---|---|
| | | | | $C_9$—aldehyde | $C_9$—alcohol | high-boiling byproducts |
| Example 7 | A' | 25 | 3.4 | 90.0 | 4.6 | 1.5 |
| Example 8 | B' | 25 | 1.7 | 91.6 | 5.1 | 1.3 |
| Example 9 | B' | 4 | 8.9 | 89.9 | 4.1 | 2.7 |
| Example 10 | B' | 3 | 11.2 | 90.0 | 4.2 | 3.3 |
| Comparative Example 4 | A' | 4 | 17.7 | 82.7 | 4.4 | 9.0 |
| Comparative Example 5 | A' | 3 | 22.1 | 78.5 | 4.0 | 14.0 |
| Comparative Example 6 | B' | 1.5 | 18.0 | 82.3 | 4.5 | 9.2 |

9. The process according to claim 6, wherein an oxide obtained by the oxidation of an olefinic compound by molecular oxygen is used as the peroxide.

10. The process according to claim 1, wherein the olefinic compound is a branched internal olefin or a mixture composed mainly of branched internal olefins.

11. The process according to claim 1, wherein the olefinic compound is a dimer of butene.

* * * * *